US009897621B2

(12) United States Patent
Andersson et al.

(10) Patent No.: US 9,897,621 B2
(45) Date of Patent: Feb. 20, 2018

(54) SAMPLE PREPARATION WORKSTATION (71) Applicant: Biotage AB, Uppsala (SE)

(72) Inventors: Lars Andersson, Uppsala (SE); Lee Williams, Newport (GB)

(73) Assignee: Biotage AB, Uppsala (SE)

( * ) Notice: Subject to any disclaimer, the term of this patent is extended or adjusted under 35 U.S.C. 154(b) by 2 days.

(21) Appl. No.: 14/913,078

(22) PCT Filed: Aug. 19, 2014

(86) PCT No.: PCT/EP2014/067614
§ 371 (c)(1),
(2) Date: Feb. 19, 2016

(87) PCT Pub. No.: WO2015/024921
PCT Pub. Date: Feb. 26, 2015

(65) Prior Publication Data
US 2016/0202277 A1    Jul. 14, 2016

(30) Foreign Application Priority Data

Aug. 21, 2013  (EP) ..................................... 13181183

(51) Int. Cl.
*G01N 35/04* (2006.01)
*G01N 35/00* (2006.01)
(Continued)

(52) U.S. Cl.
CPC .............. *G01N 35/00* (2013.01); *B01L 9/523* (2013.01); *G01N 35/0099* (2013.01);
(Continued)

(58) Field of Classification Search
CPC ... G01N 2035/0425; G01N 2035/0446; G01N 2035/00277; G01N 2035/0441;
(Continued)

(56) References Cited

U.S. PATENT DOCUMENTS 4,766,082 A    8/1988  Marteau D'Autry
6,133,045 A *  10/2000 Johnson .............. B01L 3/50255
                                               210/406
(Continued)

FOREIGN PATENT DOCUMENTS

| CH | 693689 A5 | 12/2003 |
| EP | 0180511 A1 | 5/1986 |
| EP | 2490019 A1 | 8/2012 |

OTHER PUBLICATIONS

International Search Report PCT/ISA/210 for International Application No. PCT/EP2014/067614, dated Sep. 26, 2014.

*Primary Examiner* — Justin Olamit
(74) *Attorney, Agent, or Firm* — Harness, Dickey & Pierce, P.L.C.

(57) ABSTRACT

The present invention relates to laboratory instruments, in particular to instruments for automated preparation of liquid samples like Solid Phase Extraction (SPE), Supported Liquid Extraction (SLE) or liquid-liquid extraction (LLE). The instrument reduces the risk of cross-contamination between sample collection containers by lifting the sample collection containers to the level of the outlet of the sample processing containers, or slightly above. The instrument further comprises a movable table positioning the liquid collection containers directly beneath said sample processing containers and a waste collection container directly beneath the sample processing containers, wherein said waste collection container is vertically movable from a position below the movable table to a position above the movable table.

5 Claims, 8 Drawing Sheets (51) Int. Cl.
  *B01L 9/00* (2006.01)
  *B01L 3/00* (2006.01)
  *G01N 1/40* (2006.01)

(52) U.S. Cl.
  CPC ............ *G01N 35/04* (2013.01); *B01L 3/5085* (2013.01); *B01L 3/50255* (2013.01); *B01L 2400/0409* (2013.01); *G01N 2001/4061* (2013.01); *G01N 2035/0418* (2013.01); *G01N 2035/0467* (2013.01)

(58) Field of Classification Search
  CPC ... G01N 2035/0443; G01N 2035/0444; G01N 35/04; B01L 3/5085; B01L 3/50; B01L 3/502; B01L 3/5025; B01L 3/50255
  See application file for complete search history.

(56) References Cited

U.S. PATENT DOCUMENTS

| | | | |
|---|---|---|---|
| 7,700,369 B2 * | 4/2010 | Massaro | B01L 3/50255 422/501 |
| 2012/0206713 A1 * | 8/2012 | Nogami | G01N 35/025 356/39 |

* cited by examiner

SAMPLE PREPARATION WORKSTATION

FIELD OF THE INVENTION

The present invention relates to laboratory instruments, in particular to instruments for automated preparation of liquid samples for further analysis.

BACKGROUND

Figure 1:
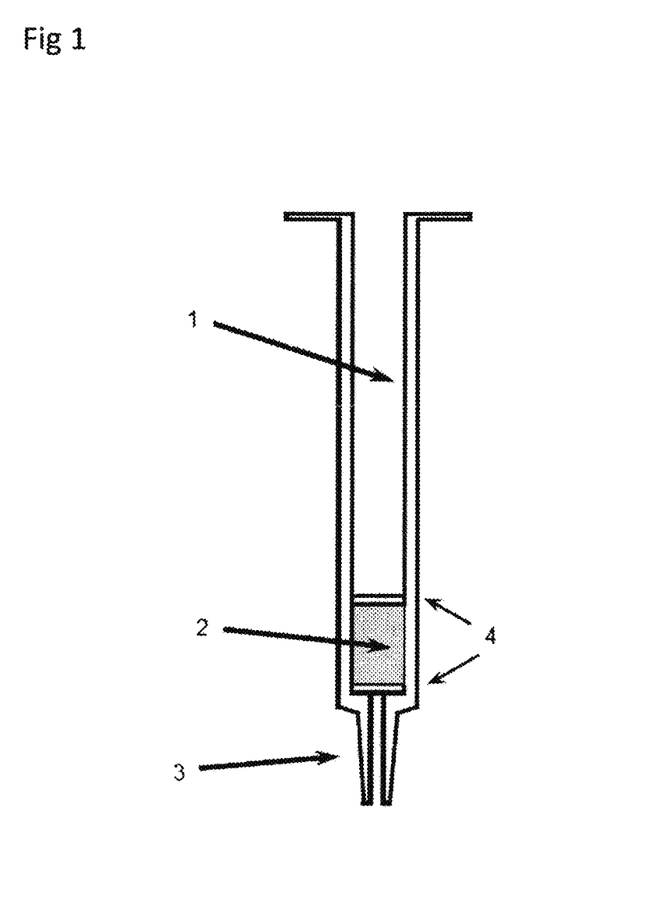
FIG. 1: Components of an SPE column. (1) Reservoir. (2) Sorbent bed. (3) Luer tip. (4) Frits (polyethylene, stainless steel, or Teflon®). Background art.

Solid Phase Extraction (SPE) is a very simple technique to use, employing disposable extraction columns or microplates (see FIG. 1) which are available in a wide range of reservoir volumes, formats and sorbents. In principle, SPE is analogous to liquid-liquid extraction (LLE). As a liquid sample passes through the SPE column, compounds are 'extracted' from the sample and adsorbed onto the support or sorbent material in the column. Interferences can then be selectively removed from the column using the correct choice of wash or interference elution solvents. Finally, the desired analytes may be selectively recovered from the column by an elution solvent, resulting in a highly purified extract. The analyte concentration in this extract is often higher than in the original sample.

Figure 2:
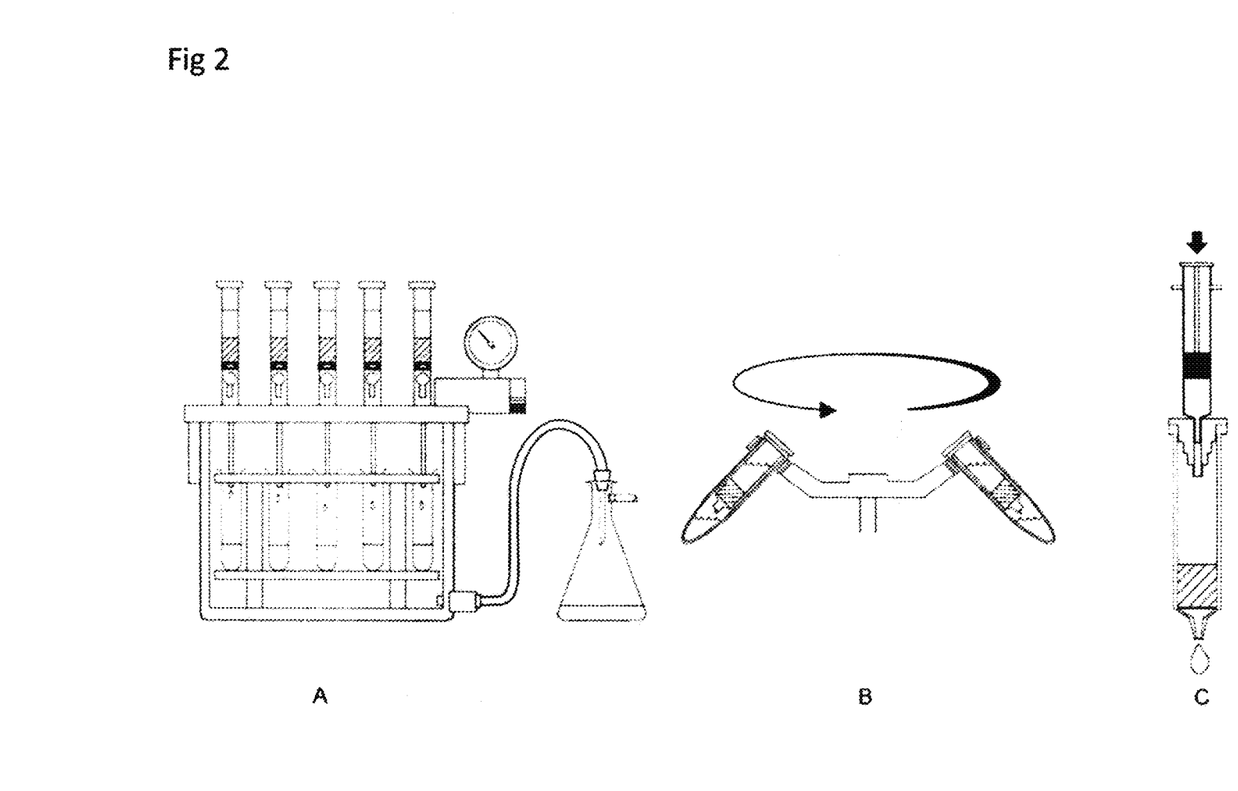
FIG. 2: Techniques for processing SPE columns. (A) Vacuum manifold. (B) Centrifugation. (C) Positive pressure (manual). Background art.

Alternatively, an extraction column may be selected that retains the interferences present in the sample, but allows the analytes to pass through un-retained, providing clean-up but not analyte trace enrichment. SPE sorbents have a typical mean particle size of 30-50 µm. Many organic solvents can flow through SPE columns or plates under gravity, but for aqueous samples and more viscous solvents, liquids must be passed through the sorbent bed using vacuum applied to the column outlet, positive pressure applied to the column inlet, or centrifugation (see FIG. 2).

The Supported Liquid Extraction (SLE) process is analogous to traditional liquid-liquid extraction (LLE) and utilizes the same water immiscible solvent systems for analyte extraction. However, instead of shaking the two immiscible phases together, the aqueous phase is immobilized on an inert diatomaceous earth based support material and the water immiscible organic phase flows through the support, alleviating many of the liquid handling issues associated with traditional LLE such as emulsion formation. As a result recoveries are often higher and demonstrate better reproducibility from sample to sample.

In sample preparation, the principles of traditional LLE (partitioning of analytes between aqueous and water immiscible organic solvents) are well known and understood. Traditionally, analytes are extracted from aqueous samples through the addition of an appropriate water immiscible organic solvent. The two immiscible phases are shaken or mixed thoroughly in a separating funnel, and based on relative solubility of the analytes in the two phases, analytes will partition into the organic solvent. The efficiency of the extraction is enhanced by the shaking, which creates a high surface area for the extraction interface allowing partitioning to occur.

Liquid-liquid extraction can give particularly clean extracts of biological fluids, since matrix components such as proteins and phospholipids are not soluble in typical LLE solvents, and are therefore excluded from the final extract. The same benefits are true for supported liquid extraction (SLE) procedures.

Because the same water immiscible solvents are used in SLE, proteins and phospholipids are efficiently removed from the final extract, and no additional steps such as protein crash (precipitation) are required. Using a fast, simple load-wait-elute procedure, SLE provides inherently cleaner extracts than other simple sample preparation techniques such as 'dilute and shoot' or protein precipitation. The efficient extraction process combining high analyte recoveries, elimination of emulsion formation, and complete removal of matrix interferences such as proteins, phospholipids, and salts results in lower limits of quantitation compared to traditional LLE.

Figure 3:
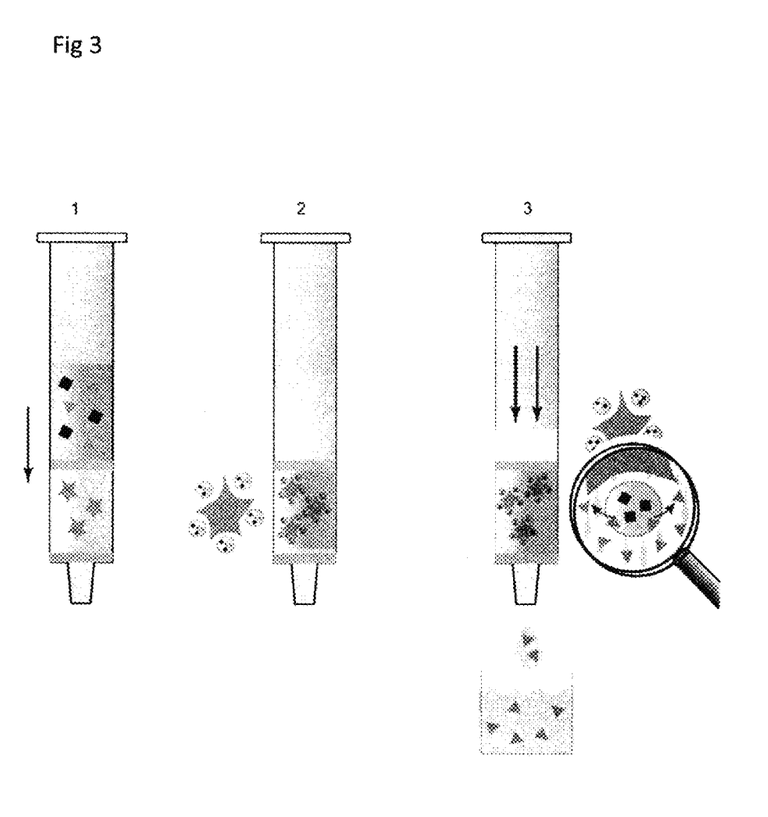
FIG. 3: Supported Liquid Extraction (SLE) mechanism. Triangles represent analyte, squares represent matrix components (e.g. phospholipids, salts, and proteins), stars represent the SLE support (diatoms). In step 1, the column is loaded. The aqueous sample then flows onto the extraction bed, and is dispersed in small droplets (step 2). In an elution step (step 3) analytes partition into elution solvent and are collected. Background art.

ISOLUTE® SLE+ products from Biotage (Uppsala, Sweden) contain a modified form of diatomaceous earth, which provides a support for the liquid-liquid extraction process to occur, but does not interact chemically with the aqueous sample. Application of the sample to the column results in the aqueous sample spreading over the surface of the material, forming an immobilized layer of small droplets held in place by a network of pores (FIG. 3). When the water immiscible extraction solvent is applied for the elution step, it flows over the aqueous droplets allowing efficient analyte partitioning. The large surface area of the extraction interface and flow through nature of the technique leads to a very efficient extraction procedure, because analytes come into contact with fresh solvent as the organic phase travels through the bed, mimicking a repeat LLE mechanism.

Processing SLE columns and 96-well plates is largely performed under gravity, with a pulse of vacuum or positive pressure used to initiate loading of the sample, and to maximize solvent recovery (leading to more reproducible analyte recovery) after elution. Both manual and automated, vacuum or positive pressure systems can be used.

A recommended workflow for processing Biotage's ISOLUTE SLE+ columns and plates is:

1. Pre-treat sample as required (including internal standard addition)
2. Ensure appropriate collection vessel is in place
3. Load sample onto ISOLUTE SLE+ column or plate
4. Apply vacuum (−0.2 bar) or pressure (3 psi) for 2-5 seconds to initiate loading
5. Wait 5 minutes for sample to completely absorb and form extraction layer
6. Apply water immiscible extraction solvent and allow to flow for 5 minutes under gravity
7. Apply vacuum (−0.2 bar) or pressure (10 psi) for 10-30 seconds to complete elution
8. Evaporate eluate to dryness and reconstitute as required.

Automated systems for transferring liquid samples between sample containers and sample processing containers are commercially available. Such systems are available e.g. from Perkin Elmer under the tradename "Janus", from Tecan Trading under the tradename "Freedom EVO", and from Tomtec under the tradename "Quadra".

Such systems generally comprise (i) a sample container for holding a sample, (ii) a solvent container for holding a solvent, (iii) a sample processing container in the form of a column or a 96-well plate comprising a sample processing material, and (iv) a liquid handling robot arranged to move an aliquot of the liquid sample from the sample container to the sample processing container, and also to move an aliquot of the solvent from the solvent container to the sample processing container.

SUMMARY OF THE INVENTION

The present invention provides an instrument for sample processing in use comprising—at least one sample container for holding at least one liquid sample;

at least one solvent container for holding at least one solvent;

at least one sample processing container comprising a sample processing material, wherein said sample processing container has an upper end with a liquid inlet opening and a lower end with a liquid outlet opening; and a liquid handling robot arranged to move an aliquot of said liquid sample from said sample container to said sample processing container, and to move an aliquot of said solvent from said solvent container to said sample processing container;

characterized in that it further comprises a moveable table arranged below the sample processing container, said table having positions for a number of liquid collection containers, whereby movement of said table in turn positions said liquid collection containers directly beneath said sample processing container;

a lift arranged to lift a liquid collection container in position beneath the sample processing container to the level of the liquid outlet opening of said sample processing container; and means for applying a positive gas pressure to the upper end of said sample processing container to push liquid contents of said sample processing container through the liquid outlet opening; into a liquid collection container.

BRIEF DESCRIPTION OF THE DRAWINGS

FIG. 5: (A) Side view of the lower level of the instrument according to the invention.

(B) Perspective view of the lower level of the instrument according to the invention.

FIG. 6: (A) Top view of a rotatable table of the lower level of the instrument according to the invention.

(B) Top view of a rotatable table of the lower level of the instrument according to the invention, having liquid collection plates in three positions and a liquid conduit plate in a fourth position.

FIG. 7: (A) Side view of the instrument
(B) Side view of the instrument in operation

DETAILED DESCRIPTION OF THE INVENTION

The aim of the present invention is to provide a relatively simple instrument that automates liquid handling in a laboratory, and especially in preparation of samples prior to analysis, with a high degree of reproducibility. Samples are automatically transferred by a disposable pipette tip from a sample container to a sample processing container, wherein the sample is processed as known in the art and described above. The processed sample is then pushed out of the sample processing container to a sample collection container. The sample collection container is then retrieved from the instrument and the sample is further analyzed using the technology of choice.

The instrument according to the present invention reduces the risk of cross-contamination between sample collection containers by lifting the sample collection containers to the level of the outlet of the sample processing containers, or slightly above. Preferably, the outlet of the sample processing container is shaped in a fashion that allows it to enter slightly into the inlet of the sample collection container. In this way, the liquid exiting one sample processing container will be collected in its designated sample collection container and the risk of liquid being diverted, by splashing or otherwise, to neighboring collection containers is greatly reduced.

The instrument according to the present invention comprises two levels. The upper level comprises at least one sample container for holding at least one liquid sample;

at least one solvent container for holding at least one solvent;

at least one sample processing container comprising a sample processing material, wherein said sample processing container has an upper end with a liquid inlet opening and a lower end with a liquid outlet opening; and a liquid handling robot arranged to move an aliquot of said liquid sample from said sample container to said sample processing container, and to move an aliquot of said solvent from said solvent container to said sample processing container.

The instrument will now be described by reference to the figures. The figures show an embodiment of the instrument using sample processing containers in a 96-well plate format. However, the instrument according to the invention may also be adapted for use with sample processing containers in the form of columns. The instrument may be designed to use such columns individually or in racks, such as racks holding 24 columns. The figures also show a preferred embodiment of the instrument wherein the moveable table of the lower level is moveable by rotation, i.e. rotatable. The table may also be arranged to be moveable in an XY-plane parallel to the bottom plate of the instrument.

Figure 4:
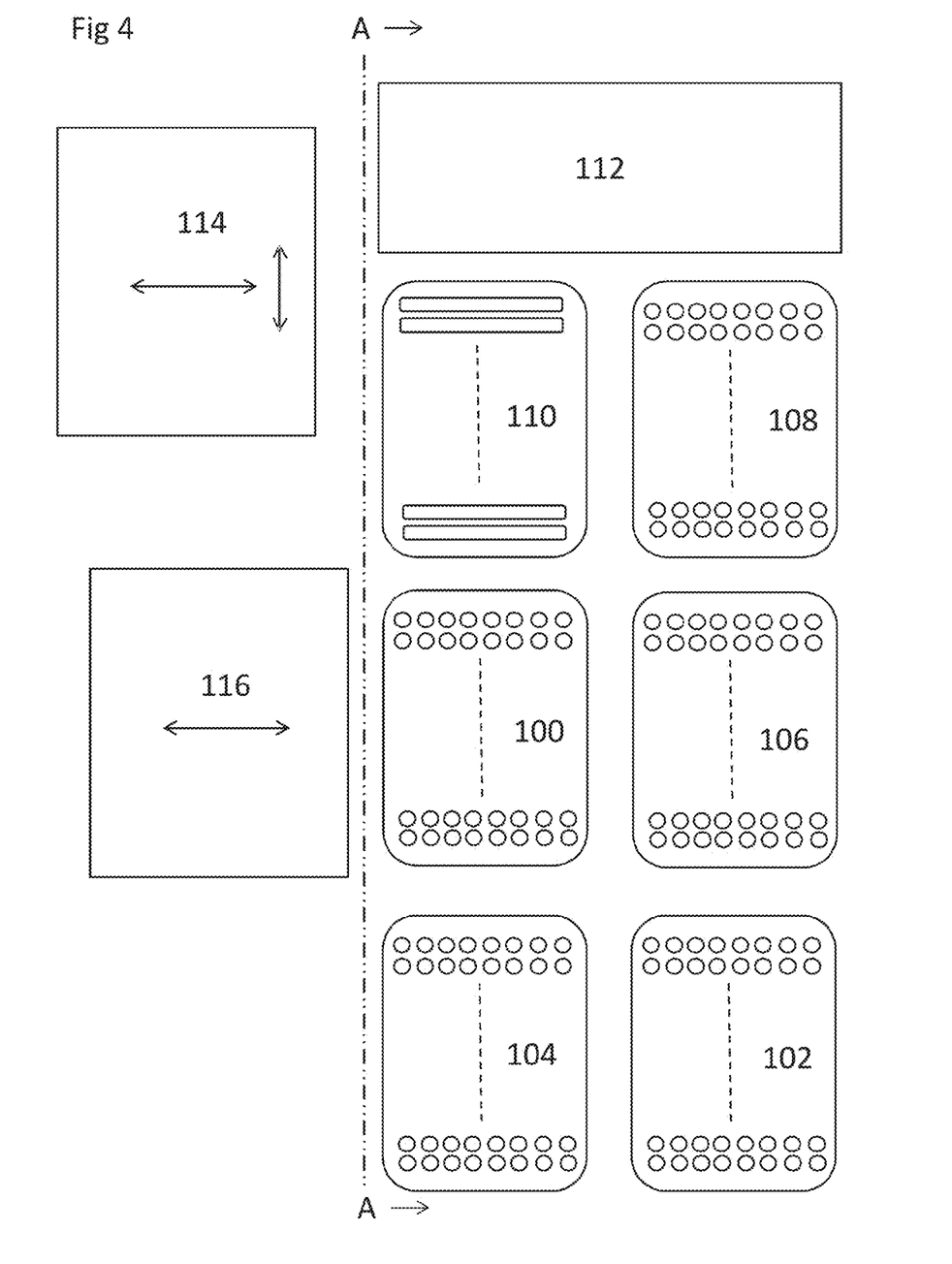
FIG. 4: A top view of the upper level of the instrument according to the invention

FIG. 4 shows a top view of the upper level of the instrument in one embodiment of the invention. In this embodiment the instrument is adapted for use with 96-well plates. In use, a 96-well filter plate (100) is inserted in the instrument. The filter plate may be a standard SLE or SPE plate. The instrument, in use, further provides a sample plate (102), a mixing plate (104), a rack for holding sample pipette tips (106), a rack for holding multi-use pipettes (108), a tray for holding solvents and/or buffers (110), and a waste tray (112) for used pipette tips. These parts of the instrument may be included in the instrument as provided to the user, or the instrument may be provided without them in order for the user to choose suitable parts adapted to the needs of the user.

The instrument further provides a pipette unit (114) suitable for transferring liquid aliquots of sample, solvent, and buffer from the respective containers to the sample processing containers. In the 96-well embodiment shown in FIG. 4, an eight-head pipette unit is suitable in order to pipette contents from one row of the 96-well plates at a time.

The pipette unit (114) is controlled by a central processing unit (not shown) and moveable in three dimensions.

Furthermore, the instrument comprises a positive pressure unit (116). The positive pressure unit (116) is moveably mounted to be able to move from a retracted position, allowing insertion of a filter plate (100) into the instrument, to an actuation position immediately above the filter plate (100). The positive pressure unit (116) is able to deliver a controlled positive pressure to each individual sample processing container, such as each well in the filter plate (100).

Figure 5:
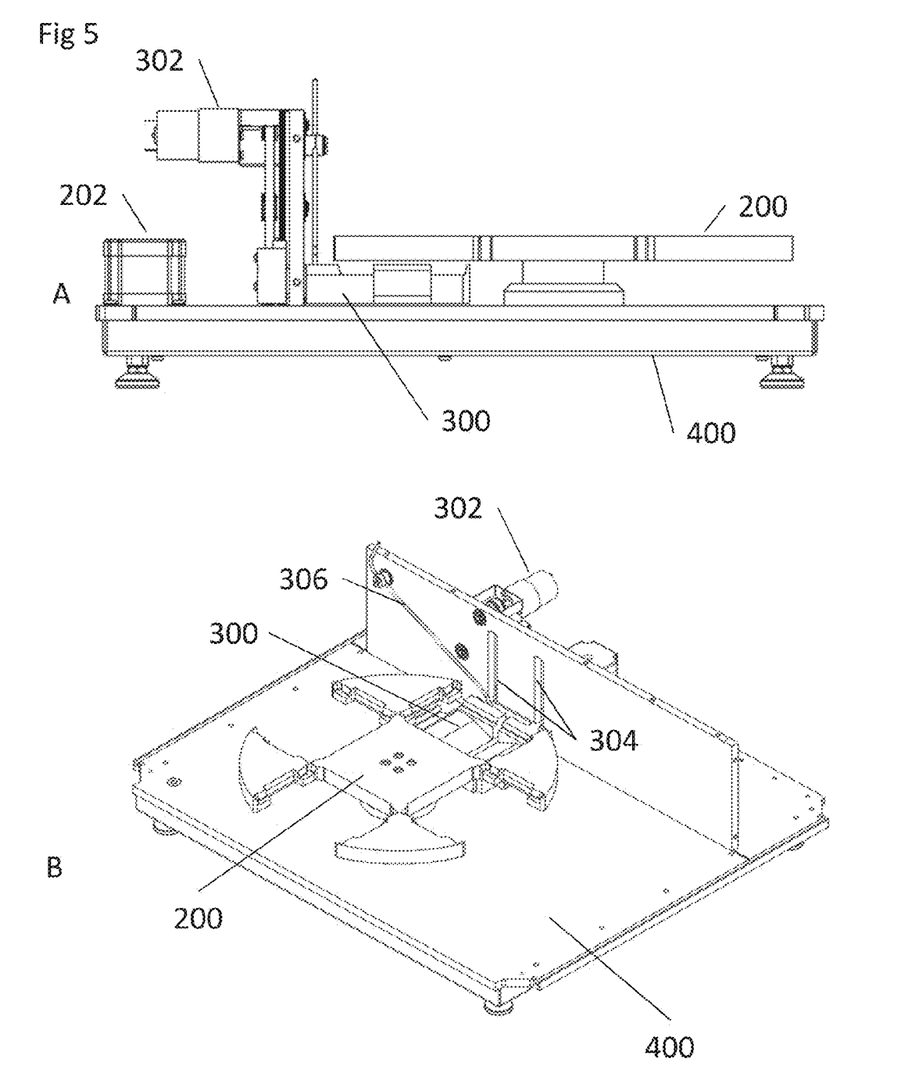

FIG. 5A shows a side view of the lower level of the instrument. This level of the instrument comprises a rotatable table (200) connected to a stepper motor (202). The stepper motor (202) drives rotation of the table (200) through any convenient transmission, such as a belt drive (not shown). The lower level also comprises a waste tray (300) that is moveable in the up-down direction. Movement of the waste tray is powered by a motor (302). The table (200) and waste tray (300) are mounted on a bottom plate (400).

FIG. 5B shows a perspective view of the lower part of the instrument. The movement of the waste tray (300) is guided by guide rails or grooves (304). The instrument may also include a waste removal conduit (306) in order to empty the waste tray (300) without the need to remove the waste tray (300).

Figure 6:
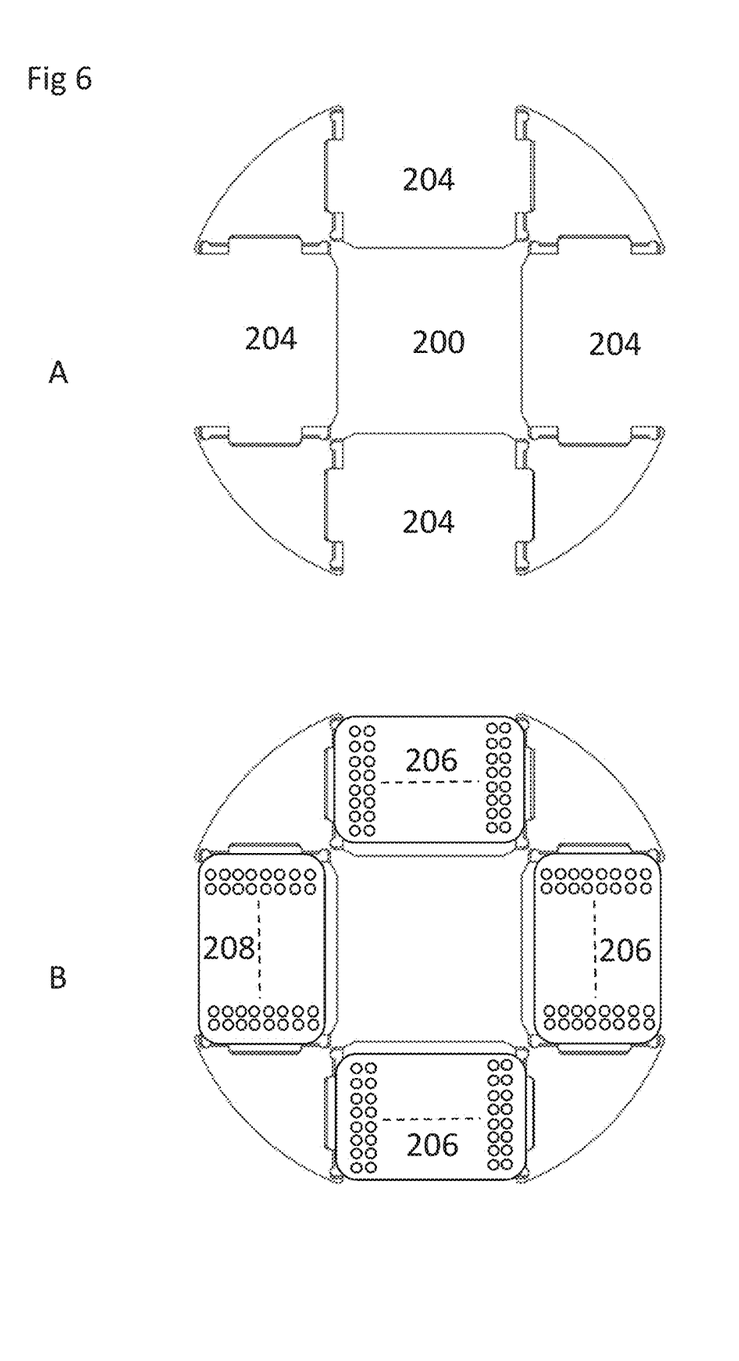

FIG. 6A shows a top view of the rotatable table (200). The table (200) has four positions (204) for receiving liquid collection plates. FIG. 6B shows a top view of the rotatable table (200) with positions (204) occupied by three liquid collection plates (206) and one liquid conduit plate (208). The liquid conduit plate (208) is of the same 96-well format as the liquid collection plates (206), but the wells are open at the bottom, facilitating transfer of liquid from the filter plate (100) through the liquid conduit plate (208) to the waste tray (300).

Figure 7A:
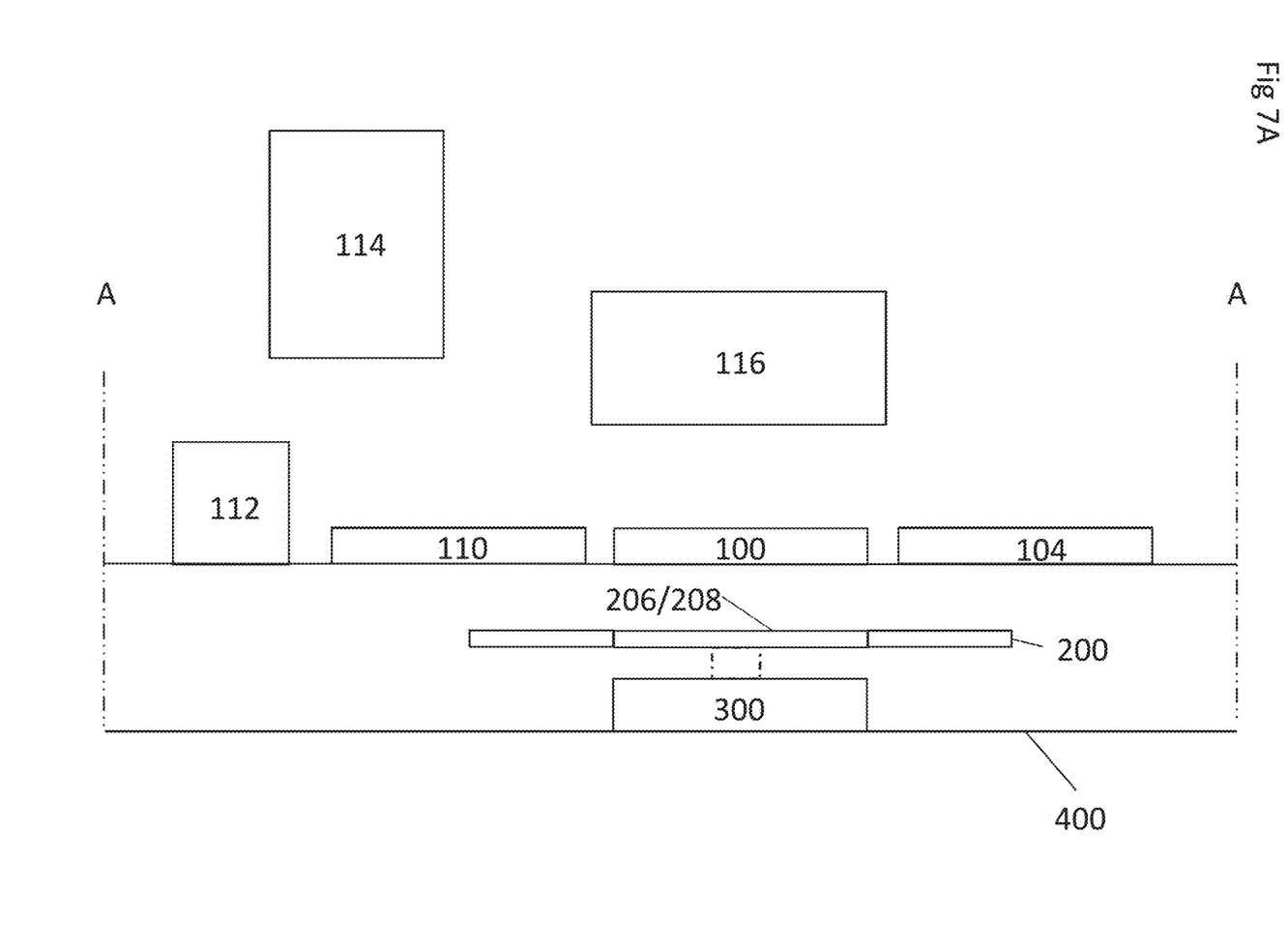
Figure 7B:
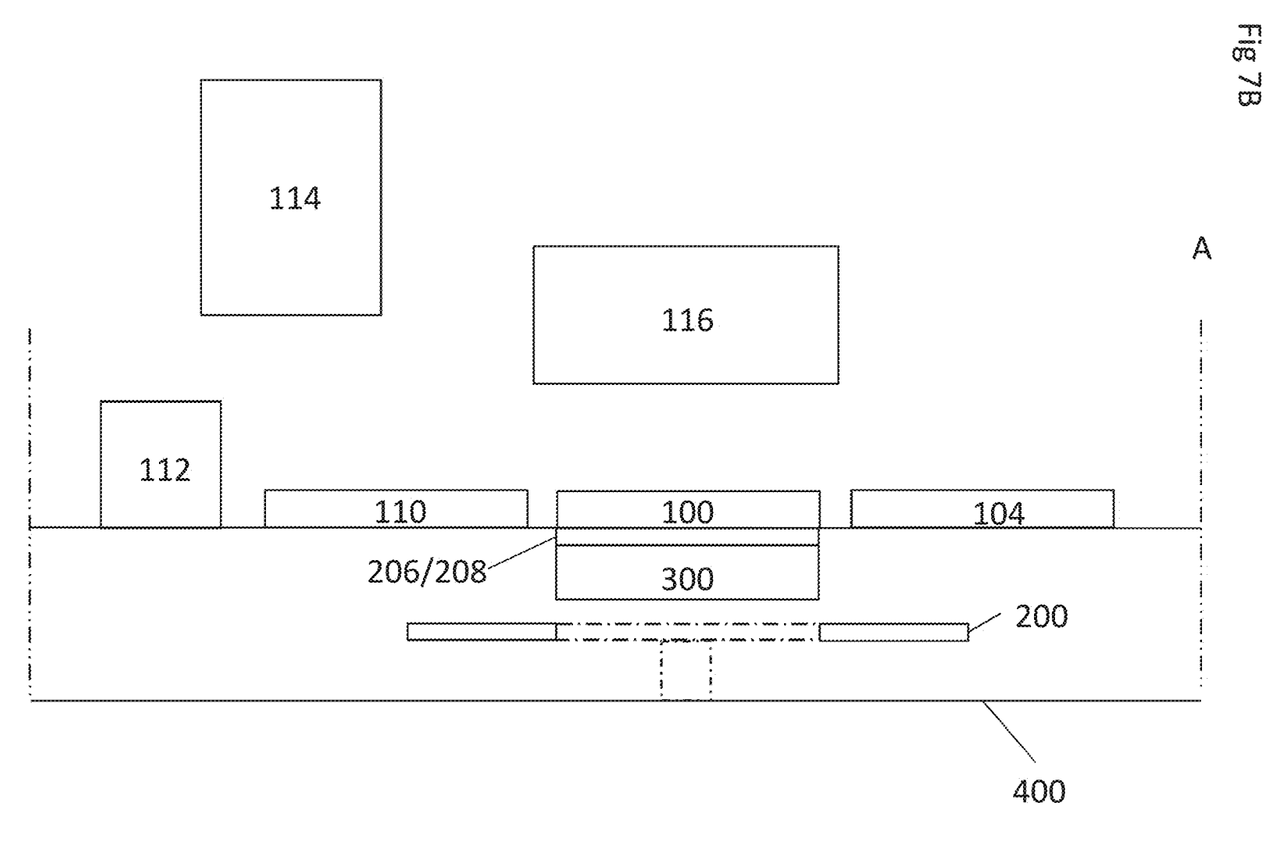

FIG. 7 show a side view of the upper and lower levels of the instrument. In FIG. 7A, the waste tray (300) is in its lower position. With the waste tray (300) in this position, the table (200) can be rotated so as to put one liquid collection plate (206) or liquid conduit plate (208) in position immediately between the waste tray (300) and filter plate (100). In FIG. 7B, the waste tray (300) is moved up to in turn push the plate (206/208) upwards so that this plate (206/208) abuts the underside of filter plate (100). The positive pressure unit (116) may then be moved into actuation position and used to apply a pressure to the wells of the filter plate (100), to thereby push liquid contained in the wells of the filter plate (100) into the plate (206/208).

If the liquid contents of the filter plate (100) comprise the analyte of interest to the user, the rotatable table (200) is rotated to put a position (204) containing a liquid collection plate (206) in position to receive the discharged liquid from the filter plate.

If, on the other hand, the discharged fluid does not comprise an analyte of interest, the rotatable table (200) is rotated to put a position (204) containing a liquid conduit plate (208) in position to receive the discharged liquid from the filter plate. The discharged liquid then passes through the liquid conduit plate (208) directly to the waste tray (300).

The invention claimed is:

1. An instrument for sample processing comprising:
   at least one sample container configured to hold at least one liquid sample;
   at least one solvent container configured to hold at least one solvent;
   at least one sample processing container including a sample processing material, wherein said at least one sample processing container includes an upper end and a lower end, said upper end including liquid inlet opening, said-lower end including a liquid outlet opening; and
   a liquid handling robot configured to move an aliquot of said at least one liquid sample from said at least one sample container to said at least one sample processing container, the liquid handling robot further configured to move an aliquot of said at least one solvent from said at least one solvent container to said at least one sample processing container;
   a moveable table below said at least one sample processing container, said moveable table including a plurality of positions configured to receive a plurality of liquid collection containers, said moveable table configured to move said plurality of liquid collection containers such that said plurality of liquid collection containers are moved to a location directly beneath said at least one sample processing container;
   a lift configured to lift at least one liquid collection container of said plurality of liquid collection containers that are directly beneath said at least one sample processing container to a level of said liquid outlet opening of said at least one sample processing container;
   a positive pressure device configured to apply a positive gas pressure to said upper end of said at least one sample processing container to push liquid contents of said at least one sample processing container through said liquid outlet opening of said at least one sample processing container into said at least one liquid collection container of said plurality of liquid collection containers; and
   a waste collection container directly beneath said at least one sample processing container, wherein said waste collection container is configured to be moved vertically from a location below said moveable table to a location above said moveable table.

2. The instrument according to claim 1, further comprising:
   a liquid conduit configured to direct a liquid flow from said liquid outlet opening of said at least one sample processing container to said waste collection container.

3. The instrument according to claim 1, wherein said moveable table is configured to rotate around a central axis of said moveable table.

4. The instrument according to claim 1, further comprising:
   a plurality of sample processing containers, said plurality of sample processing containers including at least one of
   a multi-well plate and
   a rack holding a plurality of columns; and
   wherein said plurality of liquid collection containers includes at least one of
   a multi-well plate, and
   a rack holding a plurality of columns.

5. The instrument according to claim 4, wherein,
   each individual sample processing container of the plurality of sample processing containers includes a separate, respective outlet opening; and
   the instrument further includes a plurality of liquid conduits, each liquid conduit of the plurality of liquid conduits configured to direct a separate liquid flow from a separate sample processing container of said plurality of sample processing containers to the waste collection container.

\* \* \* \* \*